US00PP27641P3

(12) United States Plant Patent
Olesen

(10) Patent No.: US PP27,641 P3
(45) Date of Patent: Feb. 7, 2017

(54) MINIATURE ROSE PLANT NAMED 'POULPAH070'

(50) Latin Name: ***Rosa* hybrid**
Varietal Denomination: Poulpah070

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 182 days.

(21) Appl. No.: 14/121,266

(22) Filed: Aug. 15, 2014

(65) Prior Publication Data

US 2016/0050810 P1 Feb. 18, 2016

(51) Int. Cl.
*A01H 5/02* (2006.01)

(52) U.S. Cl.
USPC ..... Plt./119

(58) Field of Classification Search
USPC ..... Plt./119
See application file for complete search history.

*Primary Examiner* — Keith Robinson

(57) ABSTRACT

A new garden rose plant of the Miniature class which has abundant, orange blend flowers and attractive foliage. This new and distinct variety has shown to be uniform and stable in the resulting generations from asexual propagation.

1 Drawing Sheet

Botanical designation: *Rosa* hybrid.
Variety denomination: 'Poulpah070'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpah070', originated as a single seedling from the stated cross.

The new variety may be distinguished from its male pollen parent and female seed parent by the following characteristics. The female seed parent has yellow flowers while the new variety has orange blend flowers. The male pollen parent is 15-20 cm in height, while the new variety is 25 cm in height.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah070' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpah070' was selected in the spring of 2007 by the inventor as a single plant from the progeny of the aforementioned hybridization.

Asexual reproduction of 'Poulpah070' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpah070' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah070'.

Specifically illustrated in the drawing are open flowers, stems, leaves, flower buds, and flower petals detached. Illustrated plants are 3 years of age.

DETAILED DESCRIPTION OF THE VARIETY

The following is a description of 'Poulpah070', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulpah070' in Chart 1.

CHART 1

| | 'Poulpah070' | 'Poulymp' |
|---|---|---|
| Petal Count | 35 petals | 25-30 petals |
| Flower Diameter | 55 mm | 60-70 mm |

CHART 1-continued

| | 'Poulpah070' | 'Poulymp' |
|---|---|---|
| General Tonality of Flower Color | Yellow-Orange Group 23C with other intonations of Orange Group 25C and Orange-Red Group 32B | Yellow-Orange Group 20B, Orange Group 24C, and Yellow-Orange Group 21C |

Flower and Flower Bud

Blooming habit: Continuous.

Flower bud:

*Size*.—Upon opening, 25 mm in length from base of receptacle to end of bud. Bud diameter is 13 mm.

*Bud form*.—Ovoid.

*Bud color*.—As sepals divide petals are Orange-Red Group 31B and Orange-Red Group 32A.

*Sepal inner surface*.—Color: Yellow-Green Group 144B. Surface: Lightly pubescent.

*Sepal outer surface*.—Color: Yellow-Green Group 144A with intonations of Greyed-Red Group 179A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—25 mm long by 10 mm wide.

*Receptacle*.—Texture: Smooth. Size: 6 mm in height by 10 mm wide. Color: Yellow-Green Group 144A with intonations of Greyed-Red Group 179A. Shape: Campanulate.

*Pedicel*.—Surface: Smooth. Length: 35 mm. Diameter: 2 mm on average. Color: Yellow-Green Group 144A with intonations of Greyed-Red Group 179B. Strength: Strong.

Flower bud development: Flower buds are borne in clusters of 3 flower buds per stem.

Flower bloom:

*Fragrance*.—Light floral scent.

*Duration*.—The blooms have a duration on the plant of approximately 10 days. Petals fall cleanly away from plant after flowers have fully matured.

*Size*.—Flower diameter is 55 mm when open. Flower depth is 30 mm.

*Flower shape*.—Double. General shape is a hybrid tea flower with a tight center and may overlapping petals.

*Shape of flower, side view*.—The upper portion is flat. The lower portion is flat.

Petalage: Under normal conditions, flowers have 35 petals total, 5 of which are petaloids.

General tonality of flower: Open flowers are Yellow-Orange Group 23C with other intonations of Orange Group 25C and Orange-Red Group 32B.

Petal color, open flowers:

*Outer petals*.—Upper surface: Yellow-Orange Group 14B at basal zone. Yellow-Orange Group 23C at middle zone. Orange Group 25C at margins and blended with middle zone color. Petal spot absent. Lower surface: Orange-Red Group 32C blended with Orange Group 25C. Streaks of Yellow-Orange Group 15C.

*Inner petals*.—Upper surface: Yellow-Orange Group 14B at base blended with Yellow-Orange Group 23C at middle and outer zone. Petal spot absent. Lower surface: Orange-Red Group 33C with streaks of Yellow-Orange Group 15C.

Petals:

*Petal reflex*.—Moderate to strong reflex.

*Margin*.—Entire and uniform. No undulations of margin observed.

*Shape*.—Generally rounded to elliptic. Apex shape: Rounded. Base shape: Rounded.

*Size*.—33 mm (l) 33 mm (w).

*Texture*.—Smooth on both upper and lower surfaces.

*Thickness*.—Average.

Petaloids:

*Size*.—12 mm (l) by 10 mm (w).

*Quantity*.—About 5.

*Shape*.—Elliptic. The apex has a cleft at the center of the margin. Base is acute.

*Color*.—Orange-Red Group 31A underneath with a streak of Yellow Group 15C. Upper side is Yellow-Orange Group 22A with a petal spot of Yellow Group 15C.

Reproductive organs:

*Pollen*.—None observed.

*Anthers*.—Size: 1.5 mm in length. Color: Yellow-Orange Group 22A. Quantity: 80 on average.

*Filaments*.—Color: Yellow Group 13A. Length: 5 mm.

*Pistils*.—Length: 4 mm. Quantity: 35 on average.

*Stigmas*.—Color: Greyed-Yellow Group 160A.

*Styles*.—Color: Red Group 47A.

*Location of stigmas*.—Level in location relative to the length of the filaments and the height of the anthers.

*Hips*.—None Observed.

Plant

Plant growth: Upright, bushy. Plants are 25 cm in height, and 25 cm wide.

Stems:

*Color*.—Juvenile growth: Yellow-Green Group 144B. Mature growth: Yellow-Green Group 144A.

*Length*.—On average, canes are 20 cm from the base of the plant to the flowering portion.

*Diameter*.—4 mm.

*Internodes*.—On mature canes, there is an average distance of 20 mm between nodes.

*Surface texture*.—Young wood: Smooth. Older wood: Smooth.

Long prickles:

*Incidence*.—8 prickles per 10 cm of stem.

*Size*.—Average length of prickles on mature stems is 4 mm.

*Shape*.—Upper portion is linear. Lower portion is concave.

*Color*.—Juvenile prickles: Greyed-Yellow Group 160A. Mature prickles: Greyed-Red Group 179A.

Plant foliage:

*Compound leaf*.—65 to 75 mm (l)×40 to 45 mm (w).

*Quantity*.—5 leaves per 10 cm of stem on average.

*Color of juvenile foliage*.—Upper side: Yellow-Green Group 144A. Lower side: Yellow-Green Group 144B.

*Color of mature foliage*.—Upper side: Yellow-Green Group 146A. Lower side: Yellow-Green Group 146B.

Plant leaves and leaflets:

*Stipules*.—Size: 9 mm in length. Quantity: 2 per compound leaf. Shape: Linear, slightly broad based with outward extending apices. Margins: Finely serrated. Color: Yellow-Green Group 146A.

*Petiole*.—Length: 10 to 20 mm. Diameter: 1 mm.

*Upper surface*.—Color: Yellow-Green Group 146A with intonations of Greyed-Purple Group 184A.

*Lower surface*.—Color: Yellow-Green Group 144A. Observations: Small prickles.

*Rachis*.—Length: 35 mm. Upper surface: Color: Yellow-Green Group 146A with intonations of Greyed-Purple Group 184A.

*Lower surface*.—Color: Yellow-Green Group 144A. Observations: Small prickles.

*Leaflet*.—Quantity: Normal number of leaflets leaves in middle of the stem is 5 to 7 leaflets. Margins: Serrated. Size: Average size of the terminal leaflet on normal leaves is 30 mm in length by 20 mm wide. Shape: Generally elliptical. Base: Rounded. Apex: Acute, somewhat cuspidate. Texture: Smooth on both upper and lower surfaces. Thickness: Average. Arrangement: Odd pinnate. Venation: Reticulate. Glossiness: Not glossy.

Disease resistance: Above average resistance to powdery mildew *Sphaerotheca pannosa,* downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Miniature rose class named 'Poulpah070', substantially as illustrated and described herein, due to its abundant orange blend flowers, disease resistance, and extended period of bloom.

* * * * *

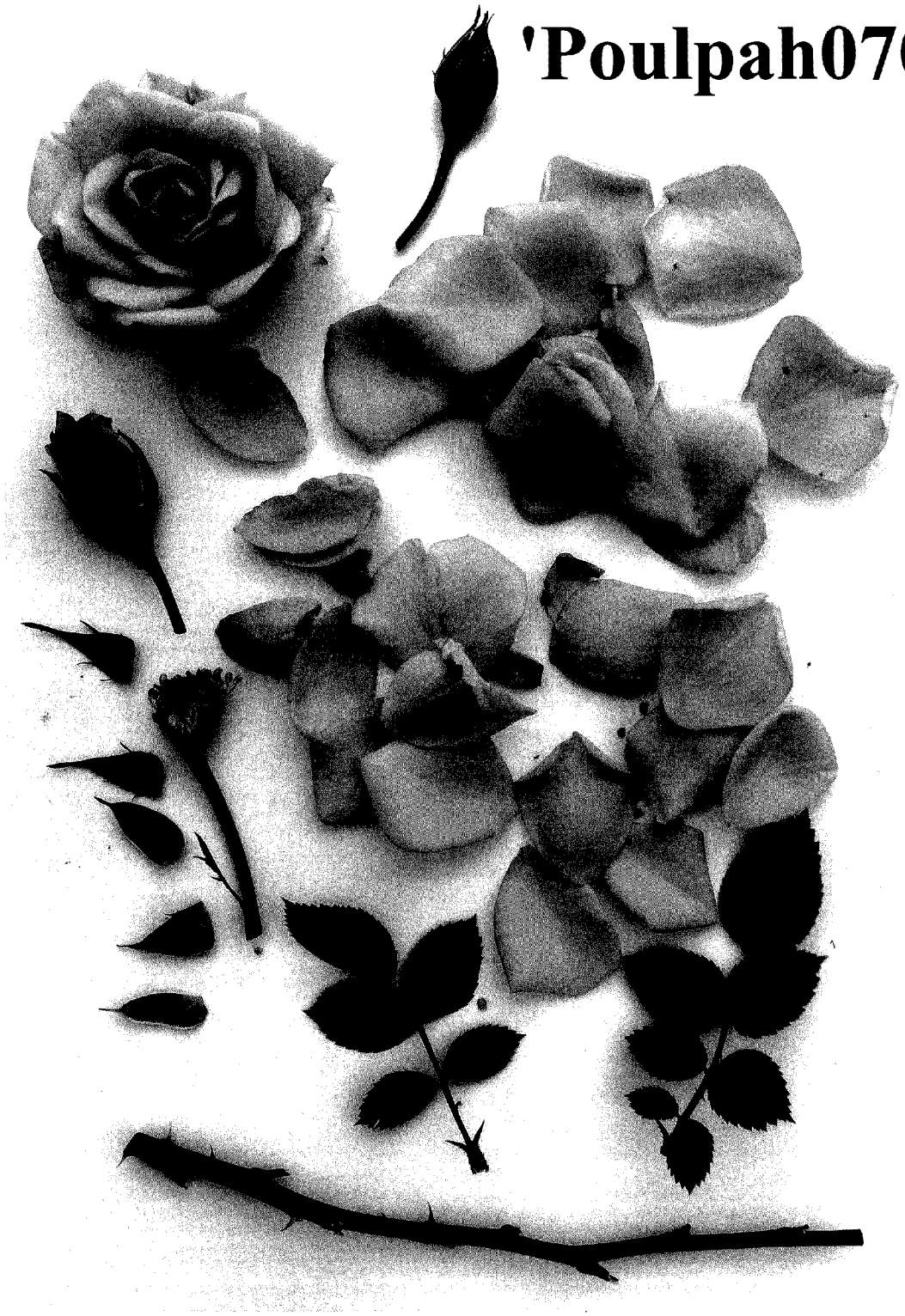
'Poulpah070'